United States Patent [19]
Gantzer

[11] Patent Number: 4,556,640
[45] Date of Patent: Dec. 3, 1985

[54] STABILIZED TEST COMPOSITION, DEVICE AND METHOD FOR THE DETERMINATION OF PEROXIDATIVELY ACTIVE SUBSTANCES

[75] Inventor: Mary Lou Gantzer, Elkhart, Ind.

[73] Assignee: Miles Laboratories, Inc., Elkhart, Ind.

[21] Appl. No.: 508,836

[22] Filed: Jun. 29, 1983

[51] Int. Cl.$^4$ .................... G01N 33/52; G01N 21/78
[52] U.S. Cl. ........................................ 436/66; 422/56; 427/2; 435/28; 436/904
[58] Field of Search ................. 422/56, 57, 73; 427/2; 435/28, 805, 810; 436/66, 95, 169, 904; 564/5

[56] References Cited

U.S. PATENT DOCUMENTS 2,981,606  4/1961  Keston ............................ 422/56 X
4,125,372 11/1978  Kawai et al. ..................... 422/56 X
4,362,697 12/1982  Tabb et al. ....................... 422/56
4,391,905  7/1983  Bauer ............................. 422/56 X

FOREIGN PATENT DOCUMENTS 3032421  4/1982  Fed. Rep. of Germany ...... 436/169
56-61999  5/1981  Japan ............................. 435/28

Primary Examiner—David L. Lacey
Assistant Examiner—Michael Gzybowski
Attorney, Agent, or Firm—Mary G. Boguslaski

[57] ABSTRACT

A test composition, device and method for determining a perioxidatively active substance in a test sample, as well as a method for preparing and using the device, are disclosed. The composition comprises an organic hydroperoxide, a benzidine indicator capable of providing a detectable response in the presence of the organic hydroperoxide and a peroxidatively active substance, and, as a stabilizing agent, an aniline chosen from pheny-1-naphthylamine, N,N-dimethylaniline and mixtures thereof. The device comprises a carrier matrix incorporated with the composition, and the method for using the device comprises contacting a test sample with the device and observing a detectable response therein. A method for preparing the device comprises preparing two or more solutions of the ingredients of the composition, wetting the carrier matrix sequentially therewith and drying the matrix after each wetting.

9 Claims, No Drawings

STABILIZED TEST COMPOSITION, DEVICE AND METHOD FOR THE DETERMINATION OF PEROXIDATIVELY ACTIVE SUBSTANCES

BACKGROUND OF THE INVENTION

1. Field of the Invention

This invention relates generally to analytical tests for the determination of peroxidatively active substances in test samples, and particularly to an improved test composition and device for such determinations having enhanced storage stability, as well as to a method for making and using the improved composition and device.

Many analytical methods are available for detecting the presence of peroxidatively active substances in biological samples such as urine, fecal suspensions and gastrointestinal contents. Hemoglobin and its derivatives are typical examples of such "peroxidatively active" substances because they behave in a manner similar to the enzyme peroxidase. Thus, such substances have also been referred to as pseudoperoxidases, i.e., enzyme-like in that they catalyze the redox reaction between peroxides and such indicator compounds as benzidine, o-tolidine, 3,3',5,5'-tetramethylbenzidine, 2,7-diaminofluorene or similar substances, thereby producing a detectable response such as color change. For example, most diagnostic assays for determining the presence of occult blood in urine rely on this pseudoperoxidase activity.

2. Background Art

The analytical test methods which, over the years, have relied on enzyme-like catalysis of the peroxidative oxidation of colorforming indicators, include wet chemical or solution procedures as well as the so-called "dip-and-read" type, reagent-bearing strip devices. Of the former, a typical example is set forth in Richard M. Henry, et al., *Clinical Chemistry Principles and Techniques*, 2nd ed., (Hagerstown, Maryland: Harper and Row, 1974), pp. 1124–1125. This procedure involves the use of glacial acetic acid (buffer), diphenylamine (indicator) and hydrogen peroxide. While such wet methods have proven analytical utility, they nevertheless have shortcomings, such as poor reagent stability and inadequate sensitivity.

Another method for the determination of peroxidatively active substances, and one presently preferred by most clinical assayists, employs the "dip-and-read", solid phase reagent strip device. Typical of such devices are those commercially available from the Ames Division of Miles Laboratories, Inc. under the trademark HEMASTIX®. They comprise, in essence, a porous paper matrix affixed to a plastic strip or handle. The matrix is impregnated with a buffered mixture of an organic hydroperoxide, for example, cumene hydroperoxide, and an indicator compound. Upon immersion in a liquid containing a peroxidatively active analyte such as hemoglobin, myoglobin, erythrocytes or other pseudoperoxidases, a blue color develops in the matrix, the intensity of which is proportional to the concentration of the analyte in the sample. By comparing the color developed in the matrix to a standard color chart, the assayist can determine, on a semiquantitative basis, the amount of the analyte which is present.

Reagent strips possess a number of advantages over wet chemistry methods, for example, greater ease of use because neither the preparation of reagents nor attendant apparatus is required, and greater comparative stability of reagents because of the dry, solid reagent state, resulting in improved accuracy, sensitivity and economy. However, a serious disadvantage of many conventional, presently-available reagent strip test devices is limited "shelf-life", i.e., lack of storage stability over prolonged periods following manufacture, resulting in markedly decreased reactivity to the presence of peroxidatively active analytes when the devices are eventually used. Thus, because analytical tools such as reagent strips usually are not used immediately after manufacture, but stored for varying periods of time before use, and because too long a period between manufacture and use of conventional reagent strips can result in severe losses of reactivity and concomitant false negative test results, enhanced shelf-life can be a marked asset: the better the shelf-life, the more reliable will be the analytical results obtained.

Conventional solid phase reagent strip devices for determining peroxidatively active substances, e.g., occult blood or hemoglobin in urine, typically utilize as an indicator system the porphyrin-catalyzed oxidation of a benzidine-type indicator, for example, o-tolidine or 3,3',5,5'-tetramethylbenzidine, by an organic hydroperoxide, such as cumene hydroperoxide. Such conventional test strips, however, are known to be particularly prone to loss of reactivity during prolonged storage, or storage at elevated temperatures—a phenomenon which is believed to be due either to volatility or chemical degradation of one or more reagent ingredients of the strip. Not only have substantial losses of reactivity been observed in such conventional reagent strips following storage at ambient temperatures, but those losses appear to be greatly accentuated, and the rate of loss accelerated, by storage at elevated temperatures. Possible explanations for the losses of reactivity in reagent strips are: (1) key ingredient(s) of the reagent composition decompose or volatilize, so that the level of ingredient(s) falls below the minimum level necessary to maintain adequate reactivity; and (2) two or more ingredients in the strip interact deleteriously, producing one or more new species which are unreactive or inhibitory.

Attempts to stabilize the reactivity of reagent compositions, and solid phase strip devices made therefrom for determining peroxidatively active substances, have followed various lines of approach. For example, U.S. Pat. No. 3,092,463 to Adams, Jr. et al., discloses an improved test composition and device for detecting occult blood in body fluids. The composition comprises an organic hydroperoxide encapsulated or entrapped in microspherical bubbles of a colloid substance, an indicator or dye precursor capable of accepting transfer of oxygen from the organic hydroperoxide to produce a color response induced by the catalytic action of the prosthetic group of hemoglobin, and a buffer for maintaining the pH of the substance being tested within the range of from 4 to 6.5. This patent discloses that the colloid substance, for example, polyvinyl alcohol, gelatin, gum arabic or carboxy vinyl polymer, can provide stabilization of the reactivity of preferred embodiments of the test device produced from the composition even after 300 hours storage at 75° C., whereas similar devices prepared without encapsulation of the hydroperoxide lost considerable reactivity after 24 hours at 50° C.

Other disclosures of stabilized test compositions and devices include the approach of U.S. Pat. No. 3,252,762 to Adams, Jr. et al., wherein the organic hydroperoxide is encapsulated in a colloidal material such as gelatin which is hardened by fixing with a dialdehyde polysaccharide. Such compositions, containing a hydroperoxide so encapsulated, a suitable indicator and a buffer, are said to exhibit enhanced stability under various adverse temperature conditions.

Still further disclosed attempts at stabilization of reagent strip devices include a recitation in *Chemical Abstracts,* Vol. 85, p. 186 (1976), describing a two-dip method for preparing reagent strips containing o-tolidine and phenylisopropyl hydroperoxide. This disclosure reports preparation of a solution of the indicator (o-tolidine.2HCl) and polyvinyl pyrrolidone in ethanol. To this solution is added a small amount of surfactant and enough citrate buffer to provide a pH of 3.7, whereafter filter paper strips impregnated with ethyl cellulose are dipped in the solution and dried. The impregnated filter paper is subsequently dipped into a second solution containing 1,4-diazabicyclo[2,2,2]octane, phenylisopropyl hydroperoxide and polyvinyl pyrrolidone, dissolved in an ethanol-toluene mixture. The thrust of this work appears directed toward stabilization of the peroxide and indicator combination through the use of the bicyclooctane derivative and the polyvinylpyrrolidone.

A similar method is disclosed in U.S. Pat. No. 3,853,471. This patent discloses the use of phosphoric or phosphonic acid amides where the substituent amido groups are primarily N-morpholine radicals.

Other approaches to stabilized reagent compositions include those of U.S. Pat. No. 4,071,317, wherein various diluent compounds, such as a mixture of dimethyl sulfone and N,N-dimethylformamide, are employed along with a hydroperoxide and an indicator; of U.S. Pat. No. 4,071,318 (use of borate esters); and of U.S. Pat. No. 4,071,321 (use of both diluents and borate esters).

Another reference of interest to these general concepts is U.S. Pat. No. 3,236,850, directed toward stabilizing organic hydroperoxides used as catalysts and oxidizing agents. This reference discloses the use of primary, secondary or tertiary amine salts with organic peroxides, and does not address the stability problems of solid phase reagent test strip devices.

A study of thermal decomposition reactions of alkyl hydroperoxides is described in J. R. Thomas, *J. Am. Chem. Soc.,* 101, pp. 246–248 (1955). The decomposition rates of four different hydroperoxides in a hydrocarbon solvent, as a function of temperature, were measured. The inclusion of phenyl-1-naphthylamine in the solution mixture was observed to produce a decrease in the rate of hydroperoxide disappearance. In addition, J. R. Thomas and O. L. Harle, *J. Phs. Chem.,* 63, pp. 1027–1032 (1959), discuss studies of the influence of solvents on the rate of decomposition of tetralin hydroperoxide. Phenyl-L-naphthylamine is disclosed as being used in these studies as a radical trap to inhibit radical chain reactions in the decomposition of the hydroperoxide.

These foregoing articles do not directly address stability problems of solid phase reagent strip devices. All of the foregoing reported studies were carried out in solution, rather than in solid-phase, the latter being the state of the hydroperoxides conventionally used in strip devices. Moreover, the solvents typically used in strip devices, e.g., dimethylformamide and acetone, are substantially different from those described in this literature: medicinal white oil, octane, decane, cyclohexane and decalin. Also, reagent strips typically contain reagents which potentially can deleteriously interact, not only with the hydroperoxide, but also with other strip ingredients.

Accordingly, despite the inherent analytical advantages of solid phase reagent strip devices over solution chemistry procedures, and the foregoing exemplary advances in the art of stabilizing the reactivity of such strip devices, the stability characteristics of the latter, particularly in the case of devices for the determination of peroxidatively active substances, are in need of even further improvement. Whereas the properties of current solid phase, state-of-the-art compositions and devices for determining peroxidatively active substances are greatly enhanced over those of wet chemical methods, and over those of methods including no stability-enhancement techniques, it would nonetheless be greatly advantageous if even more stability during prolonged storage could be afforded, eliminating "false negative" results while retaining adequate sensitivity to peroxidatively active analytes following such storage. Preferably, this should be accomplished without the need for isolation of reagents by encapsulation or similar relatively complex and expensive treatments of such compositions and devices. For example, it would be advantageous to provide suitable stabilizing agents which are readily commercially available, economical to use, and which would afford adequate sensitivity for otherwise conventional reagent/indicator systems used in solid phase test compositions and devices, as well as rendering the compositions and devices substantially more stable during long-term storage.

It is presently postulated that the frequently-observed losses of reactivity, leading to lack of storage stability or "shelf-life" of conventional solid phase reagent compositions and strip devices for determining peroxidatively active substances, may be primarily attributable to loss and/or chemical degradation of the organic hydroperoxide used in the reagent strip. Such loss or degradation may occur, for example, from decomposition or volatilization of the hydroperoxide, or chemical interaction with other strip constituents. However, it is now believed that degradation due to deleterious interaction may account for a substantial percentage of reactivity losses, although the mechanism causing such interaction is at the present unknown.

SUMMARY OF THE INVENTION

It has now been discovered, and the present invention is based upon this discovery, that present state-of-the-art, largely conventional solid phase reagent systems for determining peroxidatively active substances can be improved substantially, and the aforementioned stability problems of such systems largely alleviated, through the advantageous incorporation of certain aniline compounds in such reagent systems. Such anilines are believed to function not only as inhibitors of chain decomposition of the organic hydroperoxides commonly used in solid phase assays, but also are advantageous for diminishing or preventing deleterious interactions between reagents. These anilines can, moreover, be employed economically and with greater reliability of results, by comparison with many stabilization techniques heretofore known, such as isolation of reagents or the like.

As previously described, conventional reagent systems for determining peroxidatively active substances generally comprise an organic hydroperoxide and a redox indicator such as o-tolidine or 3,3',5,5'-tetramethylbenzidine. A peroxidatively active analyte, because it mimics the enzyme peroxidase, catalyzes or otherwise participates in a reaction between the indicator and organic hydroperoxide which yields a color, the intensity of which is indicative of the concentration of the analyte. Unlike conventional analytical reagent systems, according to the present invention an improved analytical composition is provided for determining peroxidatively active substances in a test sample; the composition not only comprises an organic hydroperoxide, an indicator capable of providing a detectable response in the presence of the organic hydroperoxide and a peroxidatively active substance, but also includes an aniline having the formula:

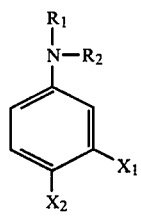

in which $R_1$ and $R_2$, same or different, are hydrogen, lower alkyl of from 1 to 6 carbon atoms, phenyl, $\alpha$-naphthyl or $\beta$-naphthyl; and in which either of $X_1$ or $X_2$ is hydrogen, $NH_2$, $NO_2$ or $NO$, the other of $X_1$ or $X_2$ being hydrogen.

Preferred anilines which can be selected for use from the foregoing class of compounds include phenyl-1-naphthylamine, N,N-dimethylaniline, o-phenylenediamine, N,N-dimethyl-3-nitroaniline, p-nitroaniline and mixtures thereof; most preferred is phenyl-1-naphthylamine and mixtures of this compound with others named.

The present invention also provides an improved analytical device for determining a peroxidatively active substance in a test sample. The device, in a preferred embodiment, comprises a carrier matrix incorporated with the improved composition of the invention. It is believed that the overall effect of the inclusion of an appropriate aniline, or mixtures of the appropriate aniline, in combination, in the composition with other, largely conventional ingredients, enables significant stabilization of reactivity and provides excellent "shelf-life" especially by comparison with conventional solid phase assays. The retention of excellent sensitivity to the presence of a peroxidatively active analyte in a test sample is enabled as well by the invention, and is, unexpectedly, comparable to that of conventional assays.

In addition, the invention provides a method for using the improved analytical device, as well as a method for producing it. In a preferred embodiment, the device is used by immersing it into a liquid test sample under analysis, and observing a detectable response, such as color change, produced therein to the presence of a peroxidatively active analyte. Preferably, the method for producing the device comprises incorporating a carrier matrix, for example a bibulous paper, with two or more solutions or suspensions comprising the reagents and other ingredients of the composition.

DETAILED DESCRIPTION OF THE INVENTION

During development of the present invention, an attempt was made to overcome the aforedescribed stability problems of conventional solid-phase reagent compositions and devices without resort to any heretofore known methodology. To this end, aniline compounds were obtained commercially; the compounds obtained were chosen to reflect substituents on the aromatic ring hypothesized to possibly exert a stabilizing effect on the various organic hydroperoxides typically used in the art. However, the mechanism by which such stabilization might be effected is, presently, unknown.

Accordingly, anilines which were determined to be suitable for use in the test composition and device of the instant invention include unsubstituted, mono-and-di-substituted anilines, and mixtures thereof, which have the general structure:

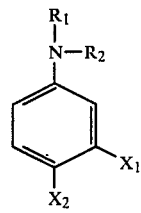

in which $R_1$ and $R_2$, same or different, are hydrogen, lower alkyl of from 1 to 6 carbon atoms, phenyl, $\alpha$-naphthyl or $\beta$-naphthyl; and in which either of $X_1$ or $X_2$ is hydrogen, $NH_2$, $NO_2$ or $NO$, the other of $X_1$ or $X_2$ being hydrogen.

Thus, according to the present invention suitable, preferred anilines include phenyl-1-naphthylamine, N,N-dimethylaniline, o-phenylenediamine, N,N-dimethyl-3-nitroaniline, p-nitroaniline, and mixtures thereof. Other suitable anilines which may be utilized to advantage in the present invention include N,N-diethylaniline, m-nitroaniline and N,N-dimethyl-4-nitroaniline. Also, mixtures of the foregoing compounds, as well as these and others within the class of compounds structurally set forth, can be used to advantage in various proportions.

Thus, it is to be appreciated that all such compounds, as herein defined structurally, are suitable for use in the present invention, although phenyl-1-naphthylamine and N,N-dimethylaniline are presently most preferred, phenyl-1-naphthylamine being most desirable. Thus, selection of any suitable particular aniline, or mixture, for use in the present invention is a matter of routine choice well within the capabilities of one of ordinary skill in the art, given the disclosure hereof.

Suitable anilines for use in the invention are either available commercially or can be readily prepared by the routineer from commercially available materials, using largely conventional organic synthesis techniques. For instance, anilines such as phenyl-1-naphthylamine as indicated in the Examples, infra, are available from Eastman Kodak Company.

The amount of a particular aniline, or mixture, which is used in a particular embodiment of the composition and device of the invention is not of critical importance, and is a matter of routine choice for one skilled in the art, in view of the instant teachings. For example, one would choose a suficient amount which would enable the chemical interactions and changes to occur, in the solid phase, which are necessary for inhibition of hydroperoxide decomposition and prevention of deleterious interaction of reagents. This would be, for example, an amount adequate—depending on the concentration and type of hydroperoxide used—to render the composition stable and sensitive to the presence of a peroxidatively active analyte to whatever extent desired in a particular analytical situation. Thus, for example, the stability desired, or necessary, can vary considerably depending on such factors as whether the analytical test (assay) is for semiquantitative or quantitative determination of an analyte; and whether the length of storage or storage temperatures are contemplated to be severely stressful. Thus, such amount can be, and preferably is, substantially 0.02 Molar (M), referred to the volume of the combined solutions of ingredients used to prepare a test device which, in a typical embodiment, would be intended for "off-the-shelf" use as an analytical tool for determining hemoglobin (occult blood) in urine, at a concentration level as low as 0.045 milligram per deciliter (mg/dL). However, it is to be appreciated that the amount of a particular aniline which may be present in compositions and devices produced according to the invention can vary widely, and that the stability and sensitivity of otherwise conventional formulations can be substantially improved by utilization of widely varying amounts of such compounds in accordance with the teachings of the invention, as set forth herein.

As previously indicated, the test composition of the invention incorporating therein, as a stabilizer, a suitable aniline, or mixture of anilines, contains at least, in addition, an organic hydroperoxide and an indicator compound which is capable, in the presence of the organic hydroperoxide and a peroxidatively active substance, of producing a detectable response. Such a detectable response can be a color change or other response detectable visually or by instrumental means.

Compositions and devices of the invention have been found to produce a response which is visually or instrumentally detectable, e.g., a color response, in the presence of hemoglobin levels in urine as low as 0.045 mg/dL. However, in addition to such utility for the detection of hemoglobin, other peroxidatively active substances which can be detected by compositions and devices of the invention include, for example, peroxidase, myoglobin, erythrocytes, and other pseudoperoxidases. Moreover, such substances can be detected by embodiments of the invention not only in urine, but in many other substances such as gastrointestinal contents, spinal fluid, industrial waste, swimming pool water and the like.

The organic hydroperoxide contemplated for use in the invention can be selected from many well known organic hydroperoxides. One selected must, however, be capable of interacting with a peroxidatively active substance in the presence of a suitable indicator to produce a detectable response, such as a color change or a change in the amount of light absorbed or reflected by the test composition. Among hydroperoxides which are particularly suitable are cumene hydroperoxide, t-butyl hydroperoxide, diisopropylbenzene hydroperoxide, 2,5-dimethylhexane-2,5-dihydroperoxide, paramenthane hydroperoxide, and other well-known hydroperoxides which are capable of oxidizing the indicator used, or mixtures of these compounds. Of the foregoing, cumene hydroperoxide is most preferred.

Many indicators are suitable for use in the invention, so long as they are capable of interaction to produce a detectable response in the presence of an organic hydroperoxide and a peroxidatively active substance. These include, for example, the so-called "benzidine-type" compounds; benzidine, o-tolidine, 3,3',5,5'-tetra(lower alkyl)benzidine, 2,7-diaminofluorene, and mixtures of these or various others. The term "lower alkyl", as used herein, refers to an alkyl radical having from 1 to 6 carbon atoms, including methyl, ethyl, n-propyl and isopropyl, and the various butyl, pentyl and hexyl isomers. However, most preferred as an indicator is 3,3',5,5'-tetramethylbenzidine.

In a preferred embodiment, the improved test composition of the invention is incorporated on or with a carrier matrix to form a solid phase, "dip-and-read" test device. Such a test device of the invention can be prepared by various well known methods, which include impregnating an absorbent matrix material with a solution or solutions of the test composition and thereafter drying the impregnated matrix, thus incorporating within the matrix a finely divided mixture of the composition ingredients. Suitable carrier matrices which can be used include paper, cellulose, wood, synthetic resin fleeces, glass fiber paper, polypropylene felt, nonwoven or woven fabrics and the like. Most suitable and preferred for use in the present invention as a carrier matrix is a bibulous paper such as filter paper. It is to be appreciated, however, that selection of an appropriate material for use as a carrier matrix is a matter of routine choice for one skilled in the art, and that the matrix can take on various physical forms, all of which are intended as being within the scope of the present invention.

The most preferred mode of preparation of a test device according to the invention is one wherein the matrix is impregnated in a two solution process. In such a preferred process, the ingredients of the composition are mixed together in two separate solutions or suspensions and the matrix is immersed, or dipped, sequentially into the solutions, and removed and dried after each immersion. The dried, impregnated matrix, following the final immersion (which, preferably, is in a solution or suspension of the aniline with a suitable organic solvent such as acetone) and final drying, can then be affixed, by suitable means such as double-sided adhesive tape, to one end of a carrier member. The carrier member can comprise, for example, an oblong plastic strip, e.g., polystyrene. The end of the strip to which the matrix is not affixed can, in this instance, serve as a handle for ease of use of the device.

In addition to the previously-described test composition ingredients which actively participate in the test reaction, further ingredients such as solvents to suspend the indicator used, thickening agents, wetting agents, buffers, emulsifying agents and other well known adjuvants can also be included in the composition. Thus, for example, as thickening agents various materials such as gelatin, algin, carrageenin, casein, albumin, methyl cellulose, polyvinyl pyrrolidone and the like can be used. As a wetting agent, it is preferable to use sodium dodecyl sulfate, but any long chained organic sulfate or sulfonate, such as dioctyl sodium sulfosuccinate or sodium dodecylbenzene sulphonate can also be used. As buffer systems, tartrate, phosphate, phthalate, citrate, acetate, succinate or other conventional buffers can be used. Preferably, the buffer system comprises sodium citrate and citric acid and the composition is buffered to a pH value of from about 5.5 to 7.0. As emulsifying agents there can be used polyvinyl alcohol, gum arabic, carboxy vinyl polymers and the like.

The organic solvents which are useful to suspend the indicator, as well as the aniline compound, include most nonreactive, organic volatile solvents with low boiling points (approximately 150° C. or less) such as dimethylformamide, acetone, chloroform, ethylene dichloride, benzene, ethyl acetate and the like, or mixtures thereof. Solvents which are not suitable include octane, decane, decalin, and others which are comparatively nonvolatile (i.e., boiling points greater than about 150° C.). It is important that selection of a particular solvent for use in the invention be predicated upon its ability to easily volatilize and thus be substantially removed in the drying process during preparation of the solid phase reagent device, so that large residues of the solvent used do not remain in the carrier matrix, which could interfere with the reactivity of the device when it is used to determine a peroxidatively active substance. Otherwise, the selection of a particular solvent is one easily made by one of ordinary skill in the art, provided with the disclosure hereof.

Other agents, such as 6-methoxyquinoline, or other activators of the peroxidase activity of hemoglobin, can also be used in the presently disclosed composition.

In use, the impregnated and dried matrix of the test device, which includes the composition of the invention, in the solid phase, can be immersed in a sample fluid or liquid suspension of the material to be tested and immediately withdrawn. In the presence of a peroxidatively active substance, contact with the sample of the solid phase test composition incorporated with the matrix gives a positive, detectable response, e.g., a color reaction which develops in the matrix. The color response can then be compared with precalibrated color standards for a quantitative estimation of the amount of peroxidatively active substance contained in the sample. Intact peroxidatively active substances, such as intact red blood cells, can appear as dots or flecks of color on the matrix. Hemolyzed red blood cells can uniformly color the matrix. In addition to visual comparison, various instrumental techniques can also be used, increasing the accuracy of the test by obviating the subjective determination of color by the human eye.

It is to be appreciated that the device of the invention can also be used to determine peroxidatively active substances not only in liquids, but in solid or semisolid substances such as feces, gastrointestinal contents and the like. Thus, for example, a thin layer of the solid or semisolid substance can be applied to the carrier matrix of the device and the detectable response, such as color change, observed in the matrix.

It has been found that the improved test composition and device of the invention are not only advantageous over conventional test compositions and devices in terms of enhanced stability, but are also highly sensitive. In a preferred embodiment, the instant test composition has been found capable of detecting hemoglobin in urine at a concentration as low as 0.045 milligram per deciliter (mg/dL), which corresponds to a blood dilution of 1:1,000,000. This degree of sensitivity is a truely unexpected advantage, and is commensurate with the sensitivity of many conventional "state-of-the-art" tests for peroxidatively active substances, demonstrating that the inclusion of an appropriate and suitable aniline compound as a stabilizer in the present test composition and device not only advantageously stabilizes reactivity under adverse storage and temperature stress, but also is not deleterious to the function of the reagent system employed therein for detecting such substances.

According to the present invention, in formulating the composition for incorporation into the matrix of a test device, in a preferred embodiment the aniline compound can be first suspended and/or dissolved in a suitable organic solvent, for example, dimethylformamide or acetone, or mixtures of these and/or other solvents, and thereafter impregnated into the matrix by immersion and drying to incorporate the aniline therewithin as previously described.

The remaining ingredients of the composition can also be incorporated with the matrix in a variety of ways to form the test device, and the preparation of such a device according to the invention is, accordingly, not limited to any particular procedure. For example, the remaining ingredients can be dissolved or suspended in a mixture of water and one or more suitable organic solvents, such as dimethylformamide, acetone, ethanol, or mixtures thereof, and such a solution or suspension can be used similarly to impregnate the matrix with these ingredients. Also, the carrier matrix can be coated with the composition, for example with a doctor blade, or can be incorporated with the composition in the form of an ink, by printing of the reagents onto the matrix.

One method presently preferred for preparing the test device is to impregnate filter paper sequentially with two different solutions or suspensions of the ingredients of the composition, the preferred solvents being distilled or deionized water, dimethylformamide (DMF) and acetone. Such impregnation can, for example, be accomplished by immersing a piece of the filter paper into a aqueous solution of buffers, wetting agents and other nonreagent ingredients, the hydroperoxide and indicator, in DMF, drying the paper in an air oven, followed by immersion of the dried paper in a second solution of the aniline compound, in acetone, and finally drying the paper. To complete the device, the dried paper is thereafter cut into a square measuring about 0.6 centimeter (cm) on a side, and the square is mounted on one end of a polystyrene film strip measuring about $0.6 \times 10$ cm. Mounting can be accomplished through use of double-faced adhesive tape, such as that commercially available from the 3M Company.

The presently most preferred method for making the device of the invention is to prepare a first aqueous solution of ingredients of the composition, comprising buffers, wetting agents and the like, and then to prepare a second organic solution comprising the hydroperoxide and indicator reagents, in DMF. These two solutions are then mixed, and a filter paper matrix is dipped, or immersed, in the mixed solutions and dried. The dried matrix is then dipped into a third solution of the aniline and a suitable solvent. The device is then completed as previously described.

EXAMPLES

The following Examples are provided in order to further demonstrate the concepts and advantages of the present invention. The Examples are intended only to be illustrative of how to make and use the invention, and are not to be interpreted as limiting its scope in any way. All percentages expressed herein are by weight, unless otherwise indicated.

EXAMPLE I

Test composition and test devices incorporating phenyl-1-naphthylamine—Three solution, two-dip procedure A first impregnating solution was prepared by combining the following ingredients in the order listed:
50 milliliters (ml) distilled water
2.13 grams (g) sodium citrate Buffer; 0.1 Molar (M)*, pH 6.9
2.77 g citric acid
6.67 g triethanolamine borate; 0.4M*
1.0 g sodium dodecyl sulfate 1.0%
0.067 g ethylenediamine tetracetic acid
A second solution was prepared by combining the following:
50 ml dimethylformamide
0.4 ml 6-methoxyquinoline; 0.4%*
4.0 ml cumene hydroperoxide
0.604 g 3,3',5,5'-tetramethylbenzidine; 0.03M*
0.108 g orange G dye
A third solution was prepared by combining the following ingredients:
0.439 g (0.02M) phenyl-1-naphthylamine
100.0 ml acetone
*Final concentration of ingredients in mixed solutions.

The first solution was thoroughly mixed with the second solution, and a sheet of laboratory filter paper (Whatman 3MM) was impregnated with the composition by dipping (immersing) it in the mixed solutions, removing the paper and then drying in an air oven at 105° C. for about 8 minutes. The dried paper was then impregnated with the third solution by dipping it therein and drying for 5 minutes at 70° C. in an air oven. The composition, comprising the ingredients of the three solutions, was thus incorporated, in the solid-phase following the latter drying, with the filter paper. A 0.6 centimeter (cm) square of the dried, impregnated paper with the composition so incorporated therewith, forming a test matrix, was then cut and applied to one end of a polystyrene film strip, measuring about 0.6 × 10 cm, using a piece of double-sided adhesive tape (3M Company).

Testing of devices of the invention produced as described above in urine samples containing various concentrations of hemoglobin yielded visually discernible colors corresponding to the hemoglobin concentration levels.

EXAMPLE II

Test composition and test devices incorporating phenyl-1-naphthylamine—Two-solution two-dip procedure A test composition was produced according to the invention substantially as described in Example I, supra, with the exception that two solutions of ingredients, rather than three, were used. The second solution comprised the hydroperoxide, the indicator and other ingredients of the second solution of Example I and, additionally, included the aniline. The first solution used was identical in ingredients, and their amounts, to the first solution of Example I, except that the volume of distilled water was increased to 100 ml. The second solution was likewise identical to the second solution of Example I, except that the volume of DMF was increased to 100 ml and 0.439 g (0.02M) of phenyl-1-naphthylamine was added. The method of making the test devices, by immersion in the solutions and drying, was substantially as described in Example I, and testing of the devices was carried out, also as previously described, in urine samples containing various concentrations of hemoglobin. As in Example I, the testing yielded visually discernible colors corresponding to the concentration levels of hemoglobin in the samples.

EXAMPLE III

Test composition and test devices incorporating N,N-dimethylaniline

A test composition was produced according to the invention substantially as described in Example II, supra, with the exception that 0.253 ml (0.02M) N,N-dimethylaniline was used in place of phenyl-1-naphthylamine. The method of preparing the test devices from the composition also was substantially as described in Example II, and testing of the devices was carried out, also as previously described, in urine samples containing various concentrations of hemoglobin. As in Example II, the testing yielded visually discernible colors corresponding to the concentration levels of hemoglobin in the samples.

EXAMPLE IV

Test composition and test devices incorporating o-phenylenediamine

A test composition was produced according to the invention substantially as described in Example I, supra, with the exception that 0.22 g (0.012M) o-phenylenediamine(dihydrochloride) was used rather than phenyl-1-naphthylamine, and 100 ml of DMF were used rather than 100 ml acetone. The method of making the test devices from the composition was substantially as described in Example I, with the exception that the paper was dried, following the second dip, for 10 minutes at 50° C. Testing of the devices was carried out, also as previously described, in urine samples containing various concentrations of hemoglobin. As in the previous Examples, the testing yielded visually discernible colors corresponding to the concentration levels of hemoglobin in the samples.

EXAMPLE V

Test composition and test devices incorporating N,N-dimethyl-3-nitroaniline

A test composition and test devices were produced according to the invention substantially as described in Example I, supra, with the exception that 0.25 g (0.02M) of N,N-dimethyl-3-nitroaniline was used rather than phenyl-1-naphthylamine in the third solution. As in the previous Examples, testing of the devices so produced was identically carried out and provided visually discernible colors corresponding to various hemoglobin concentration levels.

EXAMPLE VI

Test composition and test devices incorporating p-nitroaniline

A test composition and test devices were produced according to the invention substantially as described in Example I, supra, with the exception that 0.28 g (0.02M) of p-nitroaniline was used rather than phenyl-1-naphthylamine in the third solution. As in the previous Examples, testing of the devices so produced was identically carried out and provided visually discernible colors corresponding to various hemoglobin concentration levels.

STABILITY TESTING

Experiments were conducted to determine the "shelf-life", i.e., storage stability under ambient and elevated temperature conditions, of test devices which had been produced according to the invention as described in the Examples, supra.

A test composition, and test devices incorporating the composition in accordance with the invention, were prepared as described in Example I using 0.02M phenyl-1-naphthylamine and, in addition, control devices were prepared substantially identically to the Example I devices, but which did not utilize the third solution and phenyl-1-naphthylamine as a stabilizing agent. Following preparation, some of the devices were "stressed" by storage for four weeks in an oven at 50° C. Storage for four weeks at 50° C. was considered to correspond to storage for approximately one year at ambient temperature (about 23° C.). A set of freshly prepared strips and a set of the "stressed" strips were then dipped in urine samples known to be negative in peroxidatively active substances, and other sets were dipped in urine samples to which had been added various amounts of human whole blood. The results of visual testing of the devices for color formation (i.e., ability to detect hemoglobin in the urine samples) are set forth in the following table. The visual color readings of the devices were assigned standard solution designations (SSD) which corresponded to a color chart containing reference color blocks correlating to the colors normally produced by reaction of conventional hemoglobin test devices with standard urine samples containing the various amounts of blood. The results of this testing are presented in the following table, wherein all readings are expressed in SSD units.

TABLE I

VISUAL TEST RESULTS: CHANGE IN SSD

| Sample Hemoglobin Concentration (mg/dL) | | 0.045 | 0.135 | 0.405 |
|---|---|---|---|---|
| Example I Devices | (freshly prepared) | 23 | 32 | 40 |
| | 4 weeks at 50° C. | 15 | 28 | 35 |
| | % loss | 34.8 | 12.5 | 12.5 |
| Control Devices | (freshly prepared) | 30 | 38 | 50 |
| | 4 weeks at 50° C. | 20 | 28 | 35 |
| | % loss | 33.3 | 26.3 | 30.0 |

Additional test devices which had been prepared in accordance with the invention as described in Examples III–VI, as well as control devices which were similarly prepared, but without the use of an appropriate aniline as a stabilizing agent, were tested as previously described in urine samples containing various concentrations of hemoglobin, some after they had been freshly prepared and some after "stress" in an air oven either for four weeks at 50° C., or for 6 or 7 days at 70° C. The results of these additional tests are presented in the following tables, II through V, which further show the advantages of the invention in terms of enhancing the storage and temperature stability of the reagents utilized in the compositions and devices.

TABLE II

VISUAL TEST RESULTS: Change in SSD

| Sample Hemoglobin Concentration (mg/dL) | | 0.045 | 0.135 |
|---|---|---|---|
| Example III Devices (N,N—dimethyl-aniline, 0.02 M) | (freshly prepared) | 30 | 38 |
| | 4 weeks at 50° C. | 18 | 30 |

TABLE II-continued

VISUAL TEST RESULTS: Change in SSD

| Sample Hemoglobin Concentration (mg/dL) | | 0.045 | 0.135 |
|---|---|---|---|
| | % loss | 40 | 21.1 |
| Control Devices | (freshly prepared) | 30 | 35 |
| | 4 weeks at 50° C. | 15 | 25 |
| | % loss | 50 | 28.6 |

TABLE III

VISUAL TEST RESULTS: Change in SSD

| Sample Hemoglobin Concentration (mg/dL) | | 0.045 | 0.135 |
|---|---|---|---|
| Example IV Devices (o-phenylenediamine, 0.012 M) | (freshly prepared) | 11 | 28 |
| | 7 days at 70° C. | 10 | 12 |
| | % loss | 9 | 57 |
| Control Devices | (freshly prepared) | 30 | 38 |
| | 7 days at 70° C. | 10 | 15 |
| | % loss | 67 | 61 |

TABLE IV

VISUAL TEST RESULTS: Change in SSD

| Sample Hemoglobin Concentration (mg/dL) | | 0.045 | 0.135 |
|---|---|---|---|
| Example V Devices (N,N—dimethyl-3-nitroaniline, 0.02 M) | (freshly prepared) | 26 | 32 |
| | 6 days at 70° C. | 10 | 18 |
| | % loss | 61 | 44 |
| Control Devices | (freshly prepared) | 30 | 38 |
| | 6 days at 70° C. | 10 | 15 |
| | % loss | 67 | 61 |

TABLE V

VISUAL TEST RESULTS: Change in SSD

| Sample Hemoglobin Concentration (mg/dL) | | 0.045 | 0.135 |
|---|---|---|---|
| Example VI Devices (p-nitroaniline, 0.02 M) | (freshly prepared) | 26 | 32 |
| | 6 days at 70° C. | 10 | 20 |
| | % loss | 61 | 38 |
| Control Devices | (freshly prepared) | 30 | 38 |
| | 6 days at 70° C. | 10 | 15 |
| | % loss | 67 | 61 |

The foregoing data confirms that compositions and test devices of the invention which incorporate appropriate aniline compounds exhibit substantially enhanced stability, under adverse storage and temperature "stress" conditions, by comparison with conventional devices which do not incorporate such aniline compounds, but which incorporate identical reagents for determining peroxidatively active substances. Moreover, this enhanced stability, i.e., "shelf-life" of the composition and devices of the invention, advantageously enabled them to be more sensitive to the presence of hemoglobin even after such "stress", whereas the degradation of reactivity of the conventional control devices was comparatively greater.

It is to be appreciated that many modifications and variations of the preferred embodiments of the instant invention as set forth herein are possible without departing from the spirit and scope thereof, and that any limitations upon the invention are intended to be imposed solely by the following claims.

What is claimed is:

1. A test composition for the determination of a peroxidatively active substance in a test sample, the composition comprising an organic hydroperoxide, a benzidine indicator capable of providing a detectable response in the presence of the hydroperoxide and a peroxidatively active substance and an aniline chosen from phenyl-1-naphthylamine, N,N-dimethylaniline and mixtures thereof.

2. The composition of claim 1 in which the hydroperoxide is selected from the group consisting of cumene hydroperoxide, t-butyl hydroperoxide, diisopropylbenzene hydroperoxide, 2,5-dimethylhexane-2,5-dihydroperoxide, paramenthane hydroperoxide and mixtures thereof.

3. The composition of claim 1 in which the benzidine indicator is selected from the group consisting of benzidine, o-tolidine, 3,3',5,5'-tetra(lower alkyl)-benzidine and mixtures thereof.

4. The composition of claim 1 in which the indicator is 3,3',5,5'-tetramethylbenzidine.

5. A test composition for the determination of a peroxidatively active substance in a test sample, the composition comprising an organic hydroperoxide, 3,3',5,5'-tetramethylbenzidine and phenyl-1-naphthylamine.

6. A test device for determining the presence of a peroxidatively active substance in a test sample comprising a carrier matrix incorporated with the composition of claim 1 or 5.

7. A method for determining the presence of a peroxidatively active substance in a test sample, which method comprises the steps of contacting the sample with the device of claim 6 and observing a detectable response in the device.

8. A method for preparing a test device for determining the presence of a peroxidatively active substance in a test sample, comprising incorporating a carrier matrix with the composition of claims 1 or 5.

9. A method for preparing a test device for determining the presence of a peroxidatively active substance in a test sample, comprising the steps of:

(a) preparing a first solution comprising an organic hydroperoxide and a benzidine indicator capable of providing a detectable response in the presence of the hydroperoxide and a peroxidatively active substance;

(b) preparing a second solution comprising an aniline chosen from phenyl-1-naphthylamine and N,N-dimethylaniline and mixtures thereof and an organic solvent;

(c) incorporating the first solution with a carrier matrix by wetting the matrix with the solution;

(d) drying the wetted matrix to leave a residue of the first solution ingredients therein;

(e) incorporating the second solution with the matrix by wetting the dried matrix with the second solution; and (f) finally drying the wetted matrix to leave a residue of the second solution ingredients therein.

* * * * *